(12) United States Patent
Rucker et al.

(10) Patent No.: US 11,110,292 B2
(45) Date of Patent: Sep. 7, 2021

(54) BALANCED CONE EXCITATION FOR CONTROLLING REFRACTIVE ERROR AND OCULAR GROWTH TO INHIBIT DEVELOPMENT OF MYOPIA

(71) Applicants: Frances Joan Rucker, Boston, MA (US); Hannah Yoon, Boston, MA (US); Christopher Patrick Taylor, Quincy, MA (US)

(72) Inventors: Frances Joan Rucker, Boston, MA (US); Hannah Yoon, Boston, MA (US); Christopher Patrick Taylor, Quincy, MA (US)

(73) Assignee: New England College of Optometry, Boston, MA (US)

( * ) Notice: Subject to any disclaimer, the term of this patent is extended or adjusted under 35 U.S.C. 154(b) by 166 days.

(21) Appl. No.: 16/353,107

(22) Filed: Mar. 14, 2019

(65) Prior Publication Data
US 2019/0282828 A1    Sep. 19, 2019

Related U.S. Application Data

(60) Provisional application No. 62/644,622, filed on Mar. 19, 2018.

(51) Int. Cl.
*A61N 5/00* (2006.01)
*A61N 5/06* (2006.01)

(52) U.S. Cl.
CPC ......... *A61N 5/0613* (2013.01); *A61N 5/0622* (2013.01); *A61N 2005/0628* (2013.01); *A61N 2005/0642* (2013.01); *A61N 2005/0648* (2013.01); *A61N 2005/0651* (2013.01); *A61N 2005/0652* (2013.01); *A61N 2005/0663* (2013.01)

(58) Field of Classification Search
CPC . G02C 2202/24; A61N 5/0613; A61N 5/0622
See application file for complete search history.

(56) References Cited

U.S. PATENT DOCUMENTS

| 2013/0250235 | A1* | 9/2013 | Foulds | F21V 9/08 351/159.65 |
| 2017/0205977 | A1* | 7/2017 | Fertik | G06F 3/04842 |
| 2018/0345034 | A1* | 12/2018 | Butzloff | A61N 5/0613 |

OTHER PUBLICATIONS

Rucker et al. "Chick eyes compensate for chromatic simulations of hyperopic and myopic defocus: Evidence that the eye uses longitudinal chromatic aberration to guide eye-growth" Vision Research, vol. 49, Issue 14, pp. 1775-1783 (Year: 2009).*

(Continued)

*Primary Examiner* — Rex R Holmes
*Assistant Examiner* — Sana Sahand
(74) *Attorney, Agent, or Firm* — Anderson Gorecki LLP

(57) ABSTRACT

A myopia-inhibiting treatment device produces a therapeutic light that includes components of different wavelengths in a ratio of luminosities that creates a predetermined L-cone to S-cone excitation profile that slows ocular growth, thereby mitigating development of myopia. The components comprise blue light, green light, and red light. Therapeutic light may cause an L-cone to S-cone excitation ratio in a range between 1.38 and 0.05. In some implementations the therapeutic light causes a L-cone to S-cone excitation ratio of 0.74. In some implementations the luminosity of the combined light components is greater than 700 lux.

15 Claims, 9 Drawing Sheets

(56) References Cited

OTHER PUBLICATIONS

Rucker et al. "Cone signals for spectacle-lens compensation: Differential responses to short and long wavelengths" Vision Research, vol. 48, Issue 19, pp. 1980-1991 (Year: 2008).*

* cited by examiner

BALANCED CONE EXCITATION FOR CONTROLLING REFRACTIVE ERROR AND OCULAR GROWTH TO INHIBIT DEVELOPMENT OF MYOPIA

GOVERNMENT LICENSE RIGHTS

This invention was made with government support under Grant/Contract R01 EY023281 awarded by the National Institutes of Health. The government has certain rights in the invention.

TECHNICAL FIELD

Aspects of the present disclosure are generally related to the fields of optometry and ophthalmology, and more particularly to inhibiting development of myopia using a treatment based on controlled relative stimulation of the retinal cones.

BACKGROUND

Myopia is a condition associated with a refractive error of the eye. The condition is characterized by the eyeball having an axial length that is mismatched with the focusing power of the cornea and lens such that light rays focus at a point in front of the retina, rather than directly on the surface of the retina. Development of myopia typically begins in childhood and stabilizes in early adulthood.

At birth the human eye is often too short for its optics. This condition is called hyperopia. A hyperopic eye focuses the image of a distant object in front of the retina. With experience and development, the human eye emmetropizes and infantile hyperopia trends towards emmetropia. (Mutti, D. O., Mitchell, G. L., Jones, L. A., Friedman, N. E., Frane, S. L., Lin, W. K. & Zadnik, K. (2005). Axial growth and changes in lenticular and corneal power occur during emmetropization in infants. Investigative ophthalmology & visual science, 46(9), 3074-3080).

LCA (Longitudinal chromatic aberration) is an aberration that causes short-wavelength and long-wavelength light to be refracted by different amounts, thereby creating wavelength defocus. Wavelength defocus, in an emmetropic eye, causes shorter wavelengths to be focused in front of the retina, while longer wavelengths are focused behind the retina. In an ametropic eye, depending on the relative defocus of blue versus red light, the color contrast of the retinal image will change. If the eye is too short for its optics then blue wavelengths will be more in focus than red wavelengths, whereas if the eye is too long for its optics, red wavelengths will be more in focus than blue wavelengths. LCA and its interaction with eye length provides a cue in the retinal image that could be used by the emmetropization process to signal whether the eye is too long or too short for its optics. (Rucker, F. J., & Wallman, J. (2009). Chick eyes compensate for chromatic simulations of hyperopic and myopic defocus: evidence that the eye uses longitudinal chromatic aberration to guide eye-growth. Vision research, 49(14), 1775-1783.)

There is a correlation between time spent outdoors during childhood and a reduced incidence of myopia. (Jones, L. A., Sinnott, L. T., Mutti, D. O., Mitchell, G. L., Moeschberger, M. L., & Zadnik, K. (2007). Parental history of myopia, sports and outdoor activities, and future myopia. Investigative ophthalmology & visual science, 48(8), 3524-3532; Onal, S., Toker, E., Akingol, Z., Arslan, G., Ertan, S., Turan, C., & Kaplan, O. (2007). Refractive errors of medical students in Turkey: one-year follow-up of refraction and biometry. Optometry and Vision Science: Official Publication of The American Academy Of Optometry, 84(3), 175-180)). The decrease in myopia prevalence was not related to the amount of near work (Rose, K. A., Morgan, I. G., Ip, J., Kifley, A., Huynh, S., Smith, W., & Mitchell, P. (2008). Outdoor activity reduces the prevalence of myopia in children. Ophthalmology, 115(8), 1279-1285. https://doi.org/10.1016/j.ophtha.2007.12.019), nor to the levels of physical activity engaged in while outdoors (Guggenheim, J. A., Northstone, K., McMahon, G., Ness, A. R., Deere, K., Mattocks, C., Williams, C. (2012). Time outdoors and physical activity as predictors of incident myopia in childhood: a prospective cohort study. Investigative Ophthalmology & Visual Science, 53(6), 2856-2865). Thus, the evidence suggests that being exposed to natural light is important for the emmetropization process.

Natural light is composed of a broad-spectrum of wavelengths, whereas indoor illumination contains a greater proportion of long-wavelengths relative to short-wavelengths (i.e., more red than blue). To test the hypothesis that the difference in light spectrum is a factor in the development of myopia, Rucker et al. (Rucker, F., Britton, S., Spatcher, M., & Hanowsky, S. (2015). Blue Light Protects Against Temporal Frequency Sensitive Refractive Changes. Investigative Ophthalmology & Visual Science, 56(10), 6121-6131) used slow-frequency flicker stimuli that mimicked eye stimulation in natural light and indoor lighting. The presence of a blue light component in the natural light stimulus reduced the amount of eye growth and myopia that developed.

SUMMARY

Cones are photoreceptor cells in the retinas of the eyes of vertebrates. Different types of cones are sensitive to different wavelengths of light. The different types of cones that are present in the eye define the color vision characteristics of the eye. Cones in the human eye are normally one of three types depending on the wavelengths of light to which they are most sensitive. S-cones are most sensitive to short wavelengths of light, e.g. blue light. M-cones are most sensitive to medium wavelengths of light, e.g. green light. L-cones are most sensitive to long wavelengths of light, e.g. red light. Some aspects of the invention are predicated in part on recognition that changes in refraction and eye growth are dependent on the relative excitation of the L-cones with respect to the S-cones of the eye. All examples, aspects and features mentioned in this document can be combined in any technically possible way.

In accordance with an aspect an apparatus comprises: a myopia-inhibiting treatment device that produces a therapeutic light comprising components of different wavelengths in a predetermined ratio of luminosities that creates a predetermined L-cone to S-cone excitation profile that slows ocular growth, thereby mitigating development of myopia. In some implementations the components comprise blue light, green light, and red light. In some implementations the therapeutic light causes an L-cone to S-cone excitation ratio in a range between 1.38 and 0.05. In some implementations the luminosity of the combined lights is greater than 700 lux. In some implementations the therapeutic light causes a L-cone to S-cone excitation ratio of 0.74. In some implementations the myopia-inhibiting treatment device comprises a computer and a light source, and the light source generates the therapeutic light and the computer controls the light source. In some implementations the myopia-inhibiting treatment device comprises a lux meter that measures luminance of light generated by the light source. In some implementations the myopia-inhibiting treatment device comprises a spectroradiometer that measures spectral characteristics of the light generated by the light source. In some implementations measured luminance and measured spectral characteristics of the light generated by the light source are provided to the computer. In some implementations the computer calculates component luminosities corresponding the predetermined L-cone to S-cone excitation profile that slows ocular growth. In some implementations the computer controls the light source to generate the calculated component luminosities. In some implementations the computer controls the light source to temporally modulate the component luminosities.

In accordance with an aspect a method comprises: producing a therapeutic light comprising components of different wavelengths in a predetermined ratio of luminosities that creates a predetermined L-cone to S-cone excitation profile that slows ocular growth; and using the therapeutic light to mitigate development of myopia. In some implementations the components comprise blue light, green light, and red light, and the method comprises modulating the components to cause an L-cone to S-cone excitation ratio in a range between 1.38 and 0.05. Some implementations comprise modulating luminosity of the combined light components to greater than 700 lux. In some implementations the components comprise blue light, green light, and red light, and the method comprises modulating the components to cause an L-cone to S-cone excitation ratio of 0.74. Some implementations comprise using a computer to calculate component luminosities corresponding the predetermined L-cone to S-cone excitation profile that slows ocular growth.

In accordance with an aspect a non-transitory computer-readable storage medium comprises: calculation logic that calculates component irradiances corresponding to a predetermined L-cone to M-cone to S-cone excitation profile that slows ocular growth; and control logic that modulates components of a light source to cause an L-cone to M-cone to S-cone excitation ratio in a range between 1.38 and 0.05. In some implementations the components comprise blue light, green light, and red light, and the control logic modulates the components to cause an L-cone to S-cone excitation ratio of 0.74. Some implementations comprise power-setting logic that sets luminosity of the combined light components to greater than 700 lux.

DETAILED DESCRIPTION

Some aspects, features, and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible hardware processor components. For ease of exposition, not every step, device, or component that may be part of a computer is described herein. Those of ordinary skill in the art will recognize such steps, devices, and components in view of the teachings of the present disclosure and the knowledge generally available to those of ordinary skill in the art. The corresponding machines, steps, and processes are therefore enabled and within the scope of the disclosure.

Figure 1:
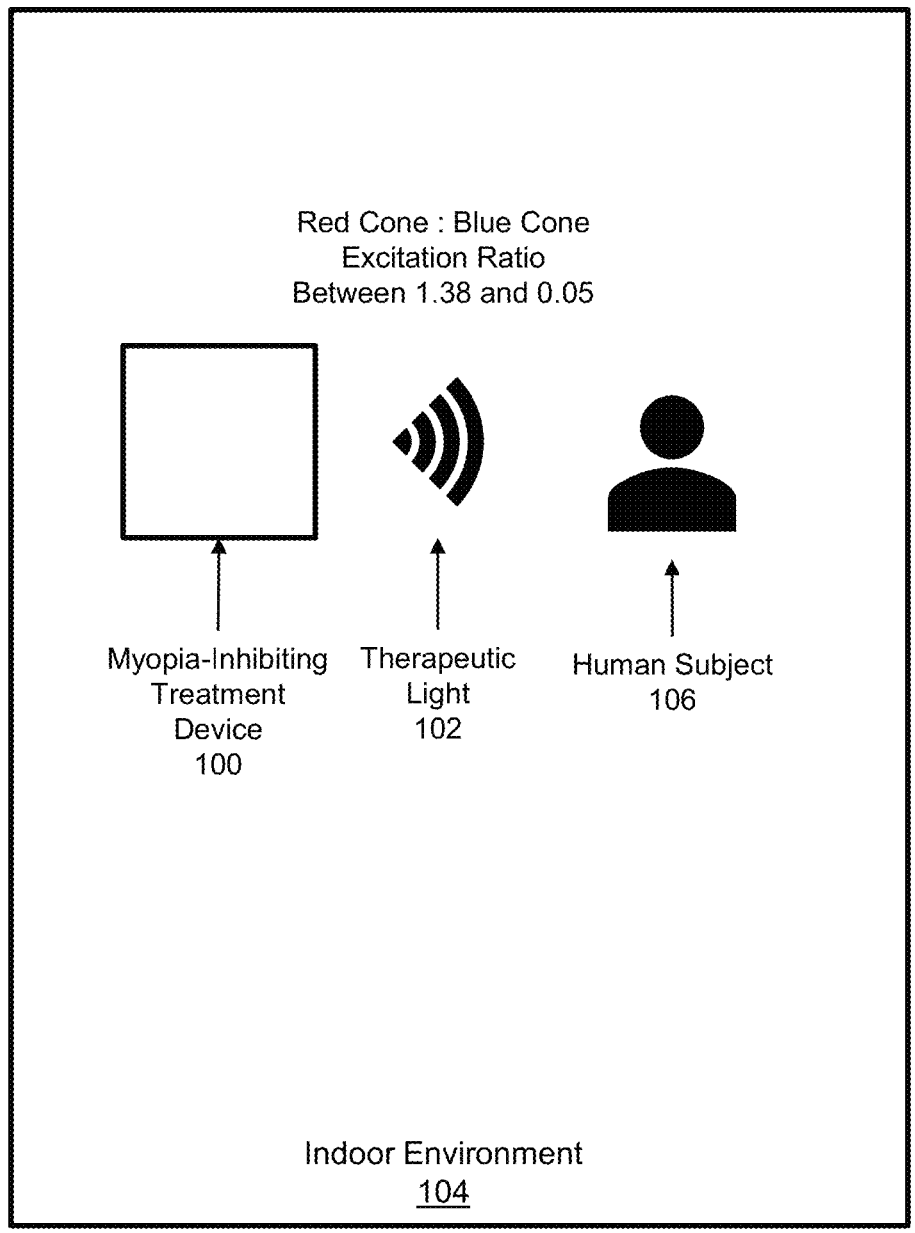
FIG. 1 illustrates a myopia-inhibiting treatment device.

Referring to FIG. 1, a myopia-inhibiting treatment device 100 produces a therapeutic light 102 that is used in an indoor environment 104 to treat a human subject 106. The treatment device uses balanced cone excitation to control refractive error and ocular growth, thereby mitigating development of myopia in the human subject. The duration and frequency of treatments may depend on a variety of factors including but not limited to pathology. Some implementations may be incorporated into devices that have functions other than treatment for myopia, e.g., lighting fixtures, computers, and mobile phones. Some implementations may be dedicated-purpose devices that are only used for treatment of myopia.

The therapeutic light 102 may include various light components of different wavelengths. For example, and without limitation, the therapeutic light may include a blue light component, a green light component, and a red light component. Each component has a predetermined or selected luminosity that may be different than the luminosity of other components. The component luminosities are in a ratio that causes a predetermined L-cone to M-cone to S-cone excitation profile, or L-cone to S-cone excitation profile, that slows ocular growth. The blue light component may provide S-cone excitation, the green light component may provide M-cone excitation, and the red light component may provide L-cone excitation. The therapeutic light may have greatest efficacy when the L-cones of the human subject 106 are stimulated 0.74 times more than the S-cones of the human subject. The therapeutic effect is lost when the L-cones are stimulated 1.38 times or more than the S-cones. The therapeutic effect is also lost when the L-cones are stimulated 0.05 or less relative to the S-cones. Therefore, a therapeutic light that provides a L-cone to S-cone excitation ratio in a range between 1.38 and 0.05 is generated in some implementations. In some implementations the luminosity of the combined light components is greater than 700 lux, e.g. and without limitation, 985 lux. Luminosity of all or some light components may be temporally varied, e.g. in a periodic manner.

Figure 2:
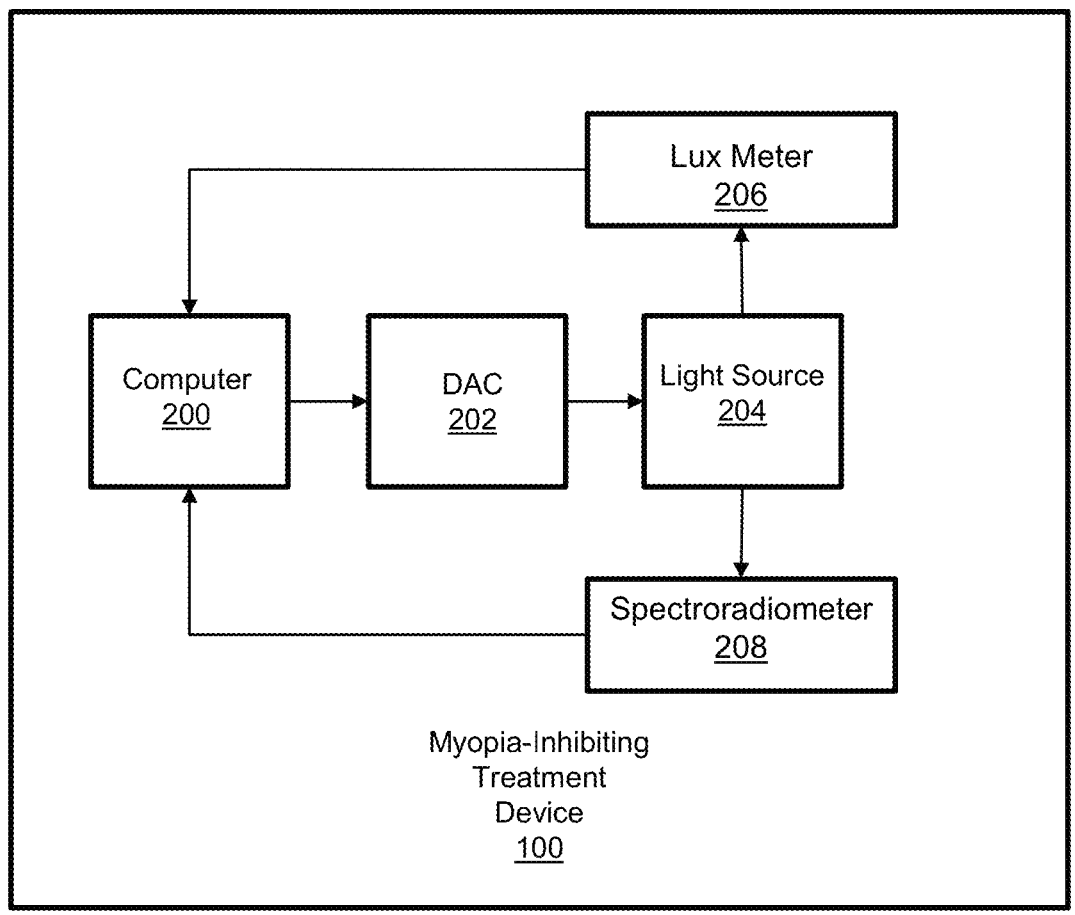
FIG. 2 illustrates an implementation of the apparatus of FIG. 1 in greater detail.

FIG. 2 illustrates an implementation of the myopia-inhibiting treatment device 100 in greater detail. The device 100 includes a computer 200, a digital to analog converter 202, a light source 204, a lux meter 206, and a spectroradiometer 208. The computer 200 includes memory and at least one processor and may be implemented with a microcontroller, dedicated-purpose computer, general purpose computer, or the computing resources of a device such as a laptop computer, tablet computer, or mobile phone, for example, and without limitation. A control signal generated by the computer 200 is provided to the light source 204 via the digital to analog converter 202. The control signal drives the light source 204 to set and adjust the characteristics of the therapeutic light. The light source may include a luminaire, bulb, lamp, monitor, device display, RGB (red, green, and blue) LEDs, or any of a wide variety of equipment. The output of the light source resulting from being driven by the control signal is measured by the lux meter 206 and the spectroradiometer 208. The lux meter measures luminance. The spectroradiometer measures spectral power characteristics. Measurements are provided in signals from the lux meter and spectroradiometer to the computer as feedback. The computer adjusts the control signal based at least in part on that feedback using logic such as a computer program to achieve the desired L-cone to S-cone or L-cone to M-cone to S-cone excitation ratio, which may be referred to herein as a balanced or "Equal" excitation or activation.

Figure 3:
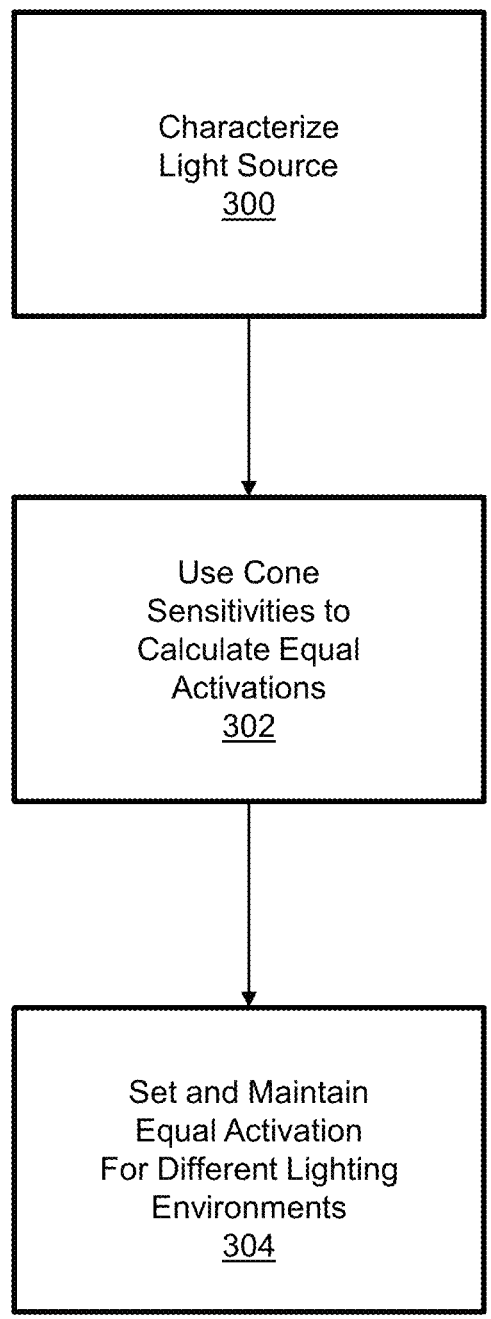
FIG. 3 illustrates a method for providing balanced cone excitation for controlling refractive error and ocular growth to inhibit development of myopia.
Figure 4:
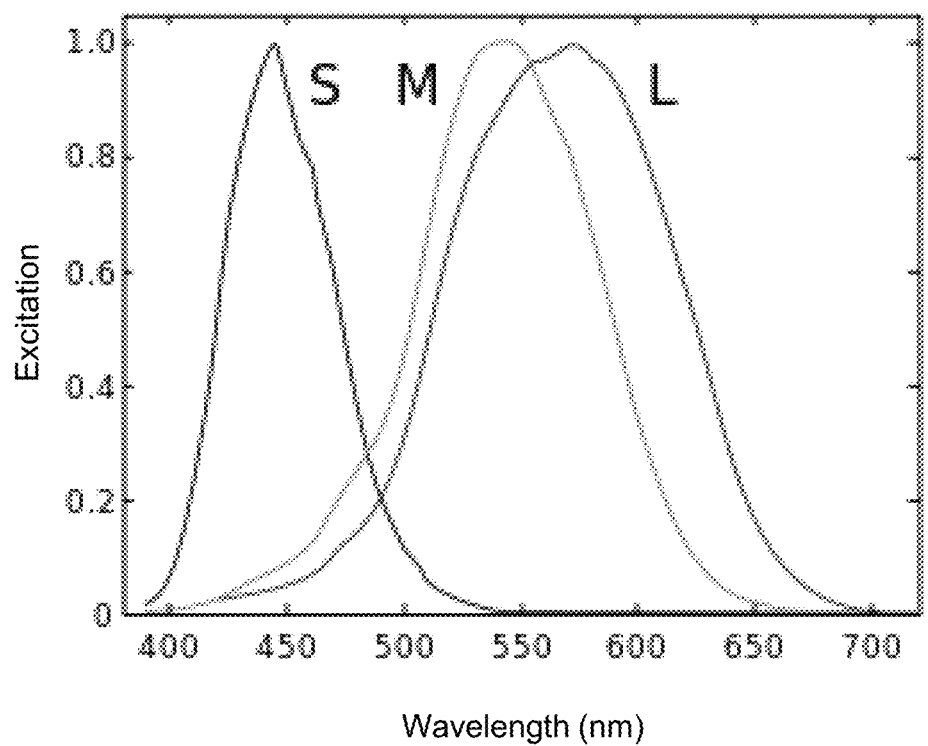
FIG. 4 illustrates spectral sensitivity curves for humans.
Figure 5A:
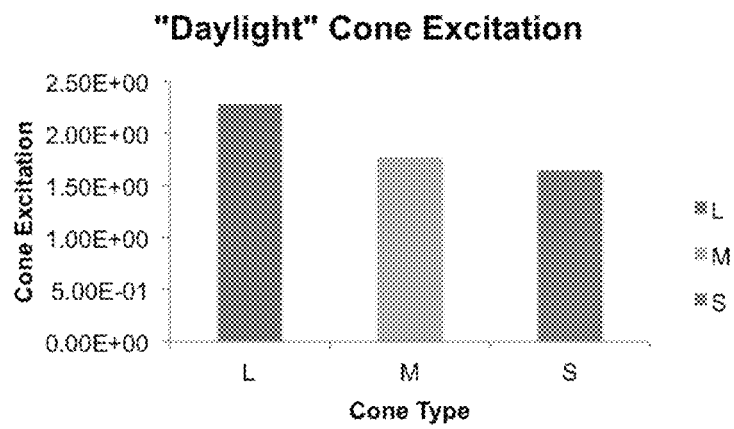
FIG. 5A illustrates L-cone, M-cone, and S-cone excitation values produced by "Daylight" light conditions.
Figure 5B:
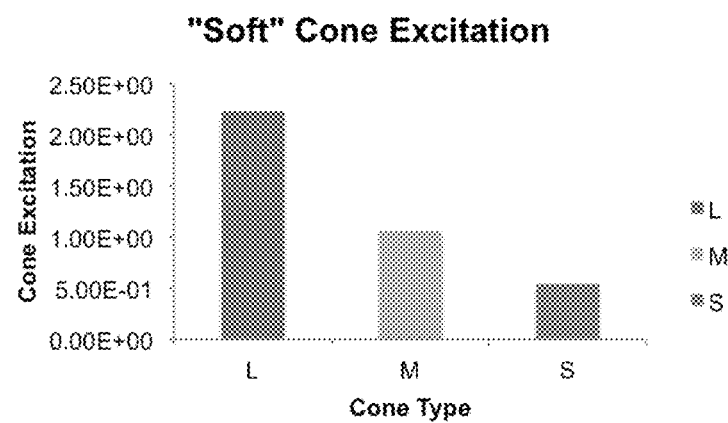
FIG. 5B illustrates L-cone, M-cone, and S-cone excitation values produced by "Soft" light conditions.
Figure 6A:
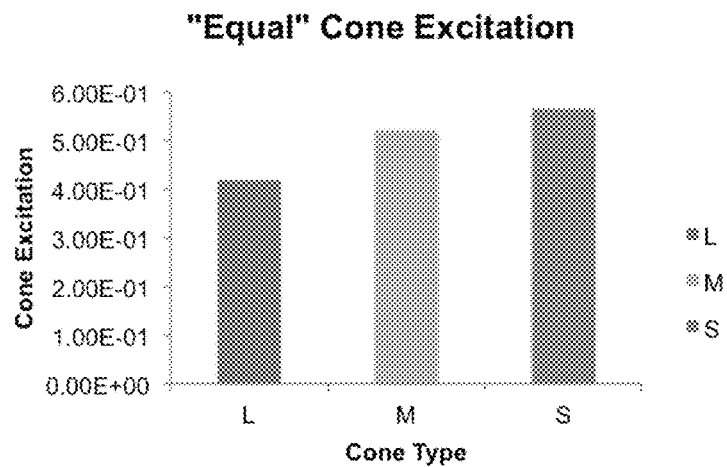
FIG. 6A illustrates L-cone, M-cone, and S-cone excitation values produced by "Equal" light conditions.
Figure 6B:
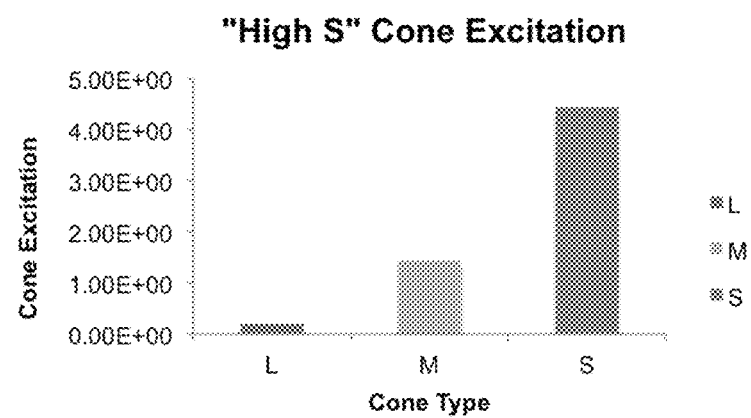
FIG. 6B illustrates L-cone, M-cone, and S-cone excitation values produced by "High S" light conditions.
Figure 7:
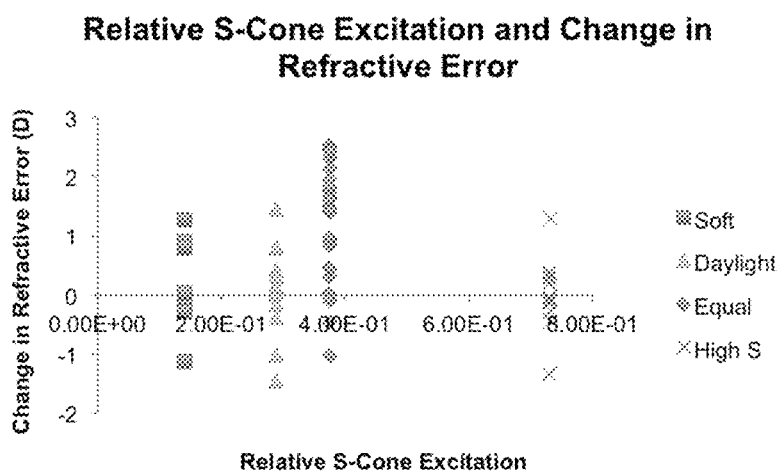
FIG. 7 illustrates S-cone excitation relative to change in refractive error in chick after 3 days of exposure.
Figure 8:
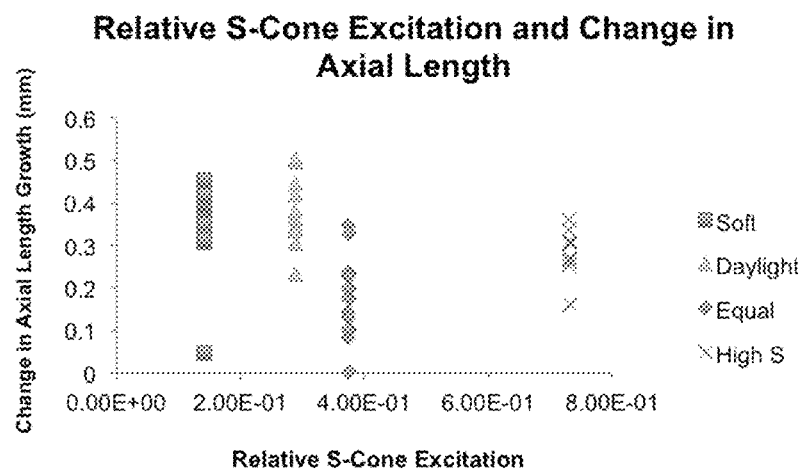
FIG. 8 illustrates S-cone excitation relative to change in axial length in chick after 3 days of exposure.
Figure 9:
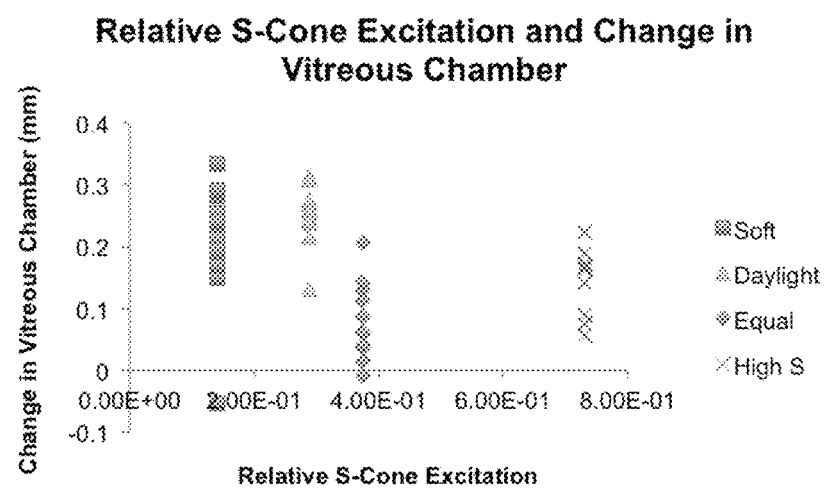
FIG. 9 illustrates S-cone excitation relative to change in vitreous chamber diameter in chick after 3 days of exposure.

FIG. 3 illustrates a method for providing balanced cone excitation for controlling refractive error and ocular growth to inhibit development of myopia with the myopia-inhibiting treatment device. Some aspects of some steps may be implemented by logic such as a computer program running on the computer. Step 300 is to characterize the light source that is used to provide the therapeutic light. The light source may be characterized in terms of luminance and spectral characteristics at various settings. The lux meter is used to measure luminance and the spectroradiometer is used to measure spectral power characteristics. Radiant power at each wavelength in a selected range, e.g. from 380 to 704 nm, may be determined and provided to the computer. More specifically, the maximum radiant power that is available at each wavelength is measured. The stimuli are then created using a fraction of the maximum available power. Step 302 is to use cone sensitivities to calculate "Equal" cone activations to produce the therapeutic effect. Measurement values outputted by the spectroradiometer may be used to calculate corresponding L-cone, M-cone, and S-cone excitation values. Cone excitation values may be calculated from spectral sensitivity curves such as those shown in FIG. 4 or derived by Rucker and Wallman (2008) (Rucker, F. J., & Wallman, J. (2008). The light energy at each wavelength is multiplied by the probability of the energy being absorbed by the cone pigments. This can be expressed mathematically as:

$$\varepsilon_i = \int_{380}^{704} Q_i(\lambda) N(\lambda)$$

Where $\varepsilon_i$ equals the excitation of the L-, M-, and S-cones, $Q_i(\lambda)$, the spectral sensitivity, of the L-, M-, or S-cones, respectively. $N(\lambda)$ is the irradiance of the light stimulus as a function of wavelength. For example, if the irradiance of a red light source measured over a range of 380-700 nm is determined to be 0.584 Wsr-1m-2, then multiplying this value by functions that describe the sensitivity of each of the cones produces a ratio of L/S cone excitation of 0.156/0.001 in a chick. Adding green light with the same irradiance would change the cone excitation ratio to 0.446/0.218 to produce a ratio of 2.05. Adding blue light to the combination would reduce the ratio further. If these lights are modulated, the desired contrast can be produced in the respective cones.

Cone signals for spectacle-lens compensation: differential responses to short and long wavelengths. Vision Research, 48(19), 1980-1991.) and Lind and Kelber (2011) (Lind, O., & Kelber, A. (2011). The spatial tuning of achromatic and chromatic vision in budgerigars. Journal of Vision, 11(7), 2-2.), both of which are incorporated by reference. Step 304 is to set and maintain the "Equal" activations for different lighting environments. The "Equal" condition may be achieved with RGB (Red, Green, Blue) light components configured to stimulate L-cone, M-cone, and S-cone excitation with an L-cone to S-cone excitation ratio between 1.38 and 0.05, e.g. 0.74. The ratio may be maintained while luminance is time-varied. For example, the luminance of all components of the light source may be modulated by the computer in a square wave pattern at 0.2 Hz-5 Hz. The maximum illuminance may be, for example and without limitation, 1790 lux, and the minimum illuminance may be, for example and without limitation, 180 lux (average luminance of 985 lux).

The increased intensity of blue light in the "Equal" lighting condition enables the eye to detect the shorter focal length of blue light which promotes a slowing of eye growth and mitigates development of myopia. The "Equal" lighting condition has been found to stimulate up to a 50% reduction in eye growth, which may account for a 1.24 D hyperopic refractive change. Reduced eye growth and hyperopic refractive changes during development may reduce the likelihood of developing myopia.

The apparatus and method were used experimentally with White Leghorn chicks (Gallus Gallus Domesticus, Cornell K strain; Cornell University, Ithaca, N.Y., USA) as test subjects. Chick cone excitations were measured for commercially available artificial illuminants and then the light sources were simulated in a controlled environment with RGB (red, green, blue) LED (light emitting diode) strips. The chick was used as a model animal system because it is a fundamental model organism for myopia development and ocular disease and it has excellent optics, color vision, and a spatial and temporal frequency sensitivity that is comparable to humans. For the experiment that will be described below, forty-nine, mixed sex, 10-day-old white leghorn chicks were randomly selected. After hatching, the chicks were raised in 12-12 light cycles in brooders with 300 lux fluorescent tubes (Philips LED tube 8.5T8/24 3500 K). Use of animals in this study was in compliance with the ARVO statement for the Use of Animals in Ophthalmic and Vision Research and was approved by the NECO Institutional Animal Care and Use Committee.

The chicks were placed in a 29-inch×16-inch wire cage illuminated by a light source of LED strips (12V LED Tape Light w/LC4 Connector-244 Lumens/ft.). Thirty-two, 0.5m, RGB LED strips were mounted 16 inches above the cage and controlled by a computer implemented as a Raspberry Pi with custom software. The LED strips were used to simulate the following lighting conditions with different ratios of short- (S), middle- (M) and long-wavelength (L) cone excitation: General Electric (GE) LED "Soft" (low S, high L), GE LED "Daylight" (medium S, high L), "Equal" (equal S, M, and L) and "High S" (high S, low L) condition. The illuminance of the light conditions was modulated in a square wave pattern at 0.2 Hz- and modulation up to 5 Hz may be used. The average illuminance in the two conditions was matched. The maximum illuminance was 1790 lux and the minimum was 180 lux (average luminance of 985 lux). The Michelson contrast of the square-wave was 80%.

The cone excitation values of the two common, commercially-available light bulbs were calculated in the following steps. First, the light bulbs were positioned 16 inches above the cage floor. A lux meter (Dr. Meter LX1010BS) was used to measure the illuminance, and a spectroradiometer (PhotoResearch PR-670) was used to determine the spectral power distribution at each wavelength from 380 to 704 nm. Next, the output values of the spectroradiometer were used to calculate the L-cone, M-cone, and S-cone excitation values. Cone excitation was calculated from spectral sensitivity curves of the chick derived by Rucker and Wallman (2008).

The "Equal" condition was created with equal RGB components of the LED to stimulate L-cone, M-cone, and S-cone excitation with an L/S cone excitation ratio of 0.74. FIGS. 5A, 5B, 6A, 6B and Table 1 show the differences in the L-cone, M-cone, and S-cone excitations produced by the illuminance conditions in chick eyes. The ratio of S-cone stimulation compared to all other cone stimulation is also shown.

TABLE 1

The L-, M-, and S-cone excitation values produced by four light conditions in chick eyes.

| Condition | L-cone | M-cone | S-cone | S/(S + M + L) | L/S ratio |
|---|---|---|---|---|---|
| "Soft" | 2.23E+00 | 1.06E+00 | 5.40E−01 | 1.41E−01 | 4.13 |
| "Daylight" | 2.28E+00 | 1.78E+00 | 1.65E+00 | 2.89E−01 | 1.38 |
| "Equal" | 4.19E−01 | 5.22E−01 | 5.65E−01 | 3.75E−01 | 0.74 |
| "High S" | 2.01E−01 | 1.43E+00 | 4.44E+00 | 7.31E−01 | 0.05 |

Using the calculated cone excitations from the light bulbs, the desired ratios of red, green, and blue light from the LED strips were calculated to mimic that of the light sources. These ratios were then used as the input for the LED strips.

Measurements

Refraction and biometry were performed pre- and post-treatment. During measurement, the chicks were anesthetized with 1.5% isofluorane in oxygen (flow rate of 2 L/min). Refractions were performed with an automated infrared photoretinoscopy (Schaeffel et al., 1987) and ocular components with an ocular biometer (Lenstar LS 900).

Procedure

Chicks were 10 days old at the start of the experiment. The cage was illuminated with the modulated light source and both eyes of the chicks were exposed to their randomly assigned illuminance condition for 3 days (Tuesday noon-Friday noon). The four illuminance conditions used were "Soft" (n=13), "Daylight" (n=12), "Equal" (n=24) and "High S" (n=10).

Analysis

The effects of the illumination conditions on the ocular components and refraction were compared based on the change between the pre- and post-condition measurements. The change in each component over the duration of the experiment with different lighting conditions was compared using Student's t-tests.

Results

Data are shown in FIGS. 5A, 5B, 6A, 6B, 7, 8, 9, and Table 2. The common commercially-available light bulbs stimulated myopic eye growth, but there was no statistically significant difference in the effects that the two conditions ("Daylight" and "Soft") had on refractive error (P=0.915; Student's t-test) and the growth of the following ocular components: axial length (P=0.368; Student's t-test), choroid (P=0.150; Student's t-test), vitreous (P=0.158; Student's t-test), and anterior chamber (P=0.7011; Student's t-test).

The mean change in refractive error in the chick eyes exposed to the "Soft" condition was +0.171±0.23 D and to the "Daylight" condition was +0.088±0.23D. The mean growth in axial length in the chick eyes was 0.339±0.028 mm and 0.377±0.023 mm for the "Soft" and "Daylight" conditions, respectively. The mean growth in choroid thickness in the chick eyes was 0.011±0.007 mm and 0.025±0.008 mm for the "Soft" and "Daylight" conditions, respectively. The mean growth in vitreous depth in the chick eyes was 0.211±0.026 mm and 0.251±0.013 mm for the "Soft" and "Daylight" conditions, respectively.

The "Equal" condition showed a greater refractive error shift towards hyperopia (+1.24±0.21D) compared to "Soft" (+0.17±0.23D, Cohen's d=1.47, t=3.37, and p<0.001) and "Daylight" (+0.08±0.23D, Cohen's d=1.30, t=3.41, p<0.001). Birds exposed to the "Equal" condition showed a reduction in axial length growth (0.183±0.029 mm) compared to "Soft" (0.340±0.028 mm, Cohen's d=1.44, t=3.44, p<0.001) and "Daylight" (0.377±0.023 mm, Cohen's d=2.01, t=4.69, p<0.001). Vitreous chamber depths were also reduced (both p<0.001). Birds exposed to the "High S" condition experienced a 54% increase in axial length growth (0.282±0.018 mm) and a 92% increase in vitreous growth (0.144±0.017 mm) compared to the "Equal" condition though refraction did not change (−0.02±0.21 D).

TABLE 2

Comparison of the mean changes in refractive error (D) and ocular component growth (mm)

|  | "Soft" | "Daylight" | "Equal" | "High S" |
|---|---|---|---|---|
| Refractive Error (D) | 0.17 ± 0.23 | 0.09 ± 0.23 | 1.24 ± 0.21 | −0.02 ± 0.21 |
| Axial Length (mm) | 0.340 ± 0.028 | 0.377 ± 0.023 | 0.183 ± 0.029 | 0.282 ± 0.018 |
| Vitreous Chamber (mm) | 0.211 ± 0.026 | 0.251 ± 0.014 | 0.075 ± 0.018 | 0.144 ± 0.017 |
| Anterior Chamber (mm) | 0.048 ± 0.022 | 0.070 ± 0.025 | −0.051 ± 0.026 | 0.036 ± 0.019 |

A ratio of L/S cone excitation of 0.74 slowed eye growth and produced less myopia than ratios of 1.38 and higher ("Soft" and "Daylight") and a ratio of 0.05 ("High S"). The L/M cone ratio had no effect on eye growth or refraction. While the spectra of common commercially-available light bulbs stimulated increased eye growth, the novel "Equal" lighting condition stimulated a 50% reduction in eye growth, which accounted for the 1.24 D hyperopic refractive changes. Reduced eye growth and hyperopic refractive changes during development reduce the likelihood of the chick developing myopia. The increased intensity of blue light in the "Equal" lighting condition enables the eye to detect the shorter focal length of blue light which promotes a slowing of eye growth and less myopia development.

What is claimed is:

1. An apparatus comprising:
  a computer;
  a light source that produces a therapeutic light in response to control signals from the computer; and
  a spectroradiometer that measures spectral characteristics of components of the therapeutic light and provides an indication of radiance of the spectral characteristics of the components of the therapeutic light to the computer;
  wherein the computer generates the control signals based on the radiance and spectral characteristics of the therapeutic light such that the therapeutic light comprises components of different wavelengths in a predetermined ratio of radiance calculated to create a balanced L-cone to S-cone excitation profile that slows ocular growth thereby mitigating development of myopia, and wherein the predetermined ratio of component radiances of the therapeutic light is calculated to create an L-cone to S-cone excitation ratio in a range between 0.74 and 1.38.

2. The apparatus of claim 1 wherein the components comprise blue light, green light, and red light.

3. The apparatus of claim 1 further comprising a lux meter that measures illumination of the combined components and provides an indication of the illumination of the combined light components to the computer, wherein the illumination of the combined components is set by the computer to be greater than 700 lux.

4. The apparatus of claim 1 wherein the ratio of radiances of the therapeutic light is calculated to create a L-cone to S-cone excitation ratio of 0.74.

5. The apparatus of claim 1 wherein the computer calculates the balanced L-cone to S-cone excitation profile based on a radiance profile and the spectral characteristics of the therapeutic light provided by the spectroradiometer, and cone sensitivities.

6. The apparatus of claim 1 wherein the computer calculates component radiances corresponding to the predetermined L-cone to S-cone excitation profile that slows ocular growth.

7. The apparatus of claim 6 wherein the computer controls the light source to generate different component radiances for different lighting environments.

8. The apparatus of claim 7 wherein the computer controls the light source to temporally modulate the component radiances.

9. A method comprising:
  producing a therapeutic light with a computer-controlled light source that uses feedback to provide radiance and spectral characteristics of components of different wavelengths of the therapeutic light, comprising:
    calculating radiances of the components and adjusting intensity of the different wavelengths to produce a predetermined balanced L-cone to S-cone excitation profile that slows ocular growth, simulating a signal that arises from longitudinal chromatic aberration, wherein the components comprise blue light, green light, and red light, that are adjusted in intensity to cause an L-cone to S-cone excitation ratio in a range between 0.74 and 1.38 and which are modulated to enhance therapeutic effect; and
    generating control signals to cause the light source to generate the therapeutic light with the calculated radiances; and
  using the therapeutic light to mitigate development of myopia.

10. The method of claim 9 comprising modulating illumination of the combined light components to greater than 700 lux.

11. The method of claim 9 wherein the components comprise blue light, green light, and red light, and comprising modulating the components to cause an L-cone to S-cone excitation ratio of 0.74.

12. The method of claim 9 comprising using a computer to calculate component radiances corresponding to the predetermined L-cone to S-cone excitation profile that slows ocular growth.

13. A non-transitory computer-readable storage medium comprising:
  calculation logic that calculates component radiances corresponding to a predetermined balanced L-cone to M-cone to S-cone excitation profile that slows ocular growth, simulating a signal that arises from longitudinal chromatic aberration; and
  control logic that modulates components of a light source to cause an L-cone to M-cone to S-cone excitation ratio in a range between 0.74 and 1.38 using feedback that controls the radiance of the components of the light source.

14. The non-transitory computer-readable storage medium of claim 13 wherein the components comprise blue light, green light, and red light, and wherein the control logic modulates the components to cause an L-cone to S-cone excitation ratio of 0.74.

15. The non-transitory computer-readable storage medium of claim 14 comprising power-setting logic that sets illumination of the combined light components to greater than 700 lux.

* * * * *